United States Patent [19]

van Dijk et al.

[11] 4,407,973

[45] Oct. 4, 1983

[54] METHANOL FROM COAL AND NATURAL GAS

[75] Inventors: Christiaan P. van Dijk, Houston; Aage Solbakken, Montgomery; Jerry M. Rovner, Houston, all of Tex.

[73] Assignee: The M. W. Kellogg Company, Houston, Tex.

[21] Appl. No.: 402,521

[22] Filed: Jul. 28, 1982

[51] Int. Cl.$^3$ .................. C07C 27/06; C07C 31/04
[52] U.S. Cl. ................................ 518/703; 518/704
[58] Field of Search .................. 518/703, 704

[56] References Cited

U.S. PATENT DOCUMENTS 4,277,416  7/1981  Grant .................................. 518/703

Primary Examiner—Howard T. Mars

[57] ABSTRACT

The present invention is directed to a process which uses the methanol synthesis gas from steam reforming in a first methanol plant and effectively integrates a second methanol plant which uses as the methanol synthesis gas (a) the purge gas from the first methanol plant and (b) the clean syn-gas produced by partial oxidation.

7 Claims, 1 Drawing Figure

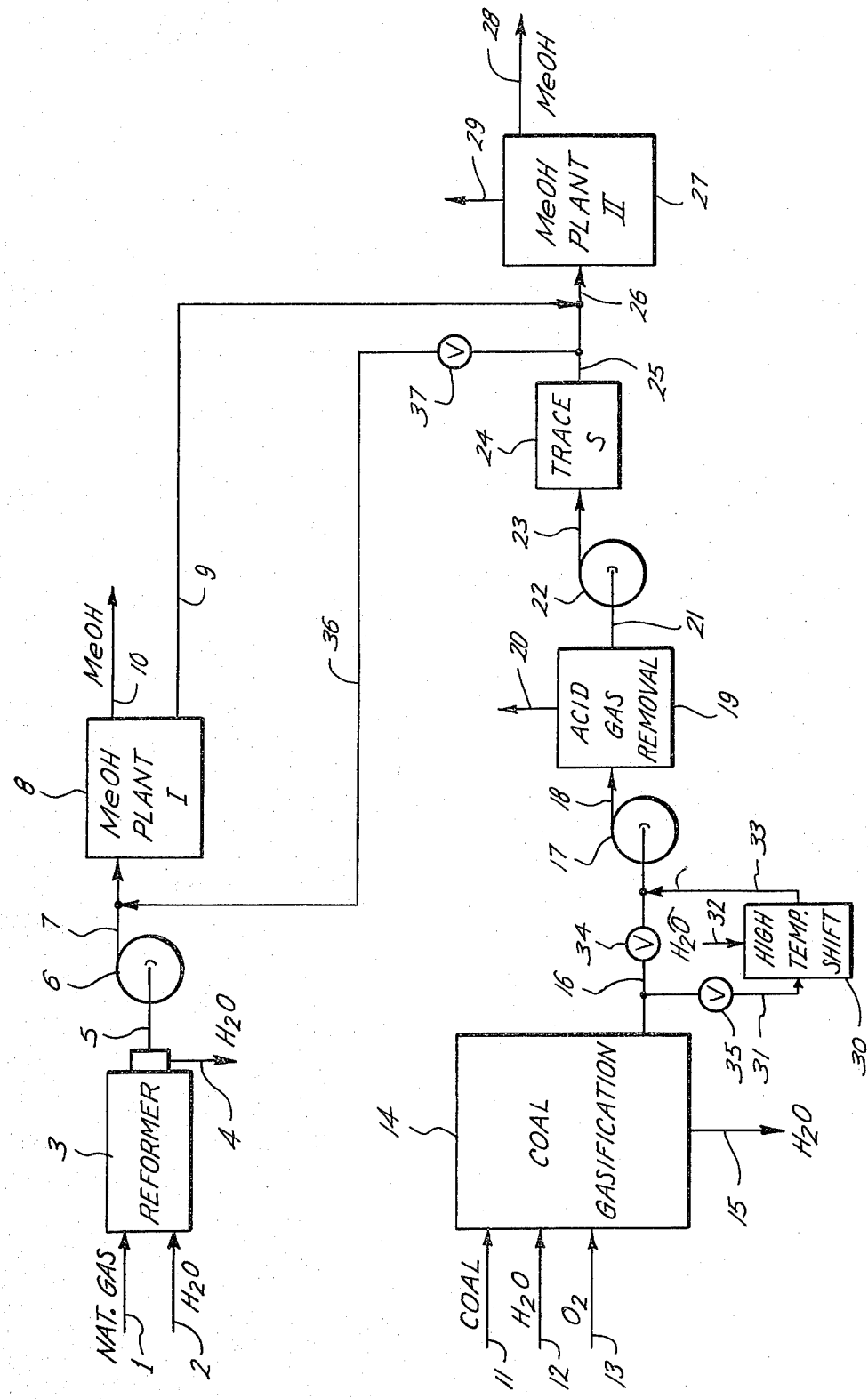

METHANOL FROM COAL AND NATURAL GAS

BACKGROUND OF THE INVENTION

This invention relates to a process for producing methanol which uses steam reforming, e.g. steam reforming natural gas, and partial oxidation, e.g. partial oxidation of coal, as sources of the methanol synthesis gas. More specifically, the present invention is directed to a process which uses the methanol synthesis gas from steam reforming in a first methanol plant and effectively integrates a second methanol plant which uses as the methanol synthesis gas (a) the purge gas from the first methanol plant and (b) the clean syn-gas produced by partial oxidation.

The prior art discloses methods for producing methanol using natural gas as the hydrocarbon feed and other methods using coal as the hydrocarbon feed.

BACKGROUND REFERENCES

The following references are incorporated into the disclosure of this patent by reference:

1-Kirk-Othmer, ENCYCLOPEDIA OF CHEMICAL TECHNOLOGY, 3rd Ed., Vol. 15, pp. 398–415, "Methanol".

2. Kirk-Othmer, ENCYCLOPEDIA OF CHEMICAL TECHNOLOGY, 3rd ed., Vol. 6, pp. 224–377, "Coal" and "Coal Conversion Processes".

3. Kirk-Othmer, ENCYCLOPEDIA OF CHEMICAL TECHNOLOGY, 2nd Ed., Vol. 10, pp. 353–442, "Gas, Manufactured".

4. U.S. Pat. No. 4,277,416 which discloses a single methanol plant which is fed by clean syn-gas from coal gasification and syn-gas from natural gas.

The following references are included as being of interest:

U.S. Pat. Nos.
3,501,516
3,920,717
3,940,428
3,962,300
3,972,958
3,993,457
4,065,483
4,076,761
4,203,915
4,219,492
4,238,403

SUMMARY OF THE INVENTION

The present invention is directed to a process for producing methanol which integrates a first methanol plant with a second methanol plant. The first methanol plant is designed to use a synthesis gas produced by steam reforming a methane-rich gas. The second methanol plant is designed to use as the methanol synthesis gas (a) the purge gas from the first methanol plant and (b) the clean syn-gas obtained from the partial oxidation of a heavy carbonaceous material, such as coal. The integration of two methanol plants according to the present invention provides an improved process which employs the unit operations of steam reforming and partial oxidation to convert different hydrocarbon feeds into methanol synthesis gas and has a total capacity between 1.45 and 1.75 of the design capacity of the first methanol plant, based on methane-rich gas alone.

More specifically, the present invention is directed to a process for producing methanol which comprises converting a methane-rich gas by steam reforming into a mixture comprising hydrogen and carbon oxides and reacting said mixture in a first methanol plant which produces a methanol stream and a purge gas stream, the improvement to produce a total capacity of methanol between 1.45 and 1.75 of the design capacity of the first methanol plant comprising:

(a) converting by high temperature partial oxidation using essentially pure oxygen a heavy carbonaceous material into a mixture of gases comprising hydrogen, carbon monoxide, carbon dioxide, other acid gases and hydrocarbons;

(b) removing said other acid gases and trace elements of sulfur to produce a clean syn-gas; and (c) reacting said purge gas and said clean syn-gas in a second methanol plant to produce a second methanol stream.

DESCRIPTION OF THE DRAWING

The FIGURE is a block flow diagram of the present invention.

DETAILED DESCRIPTION OF THE PREFERRED EMBODIMENTS

Normally, methanol is produced by the catalytic conversion of a methanol synthesis gas mixture containing hydrogen and carbon oxides at elevated pressure. The catalytic conversion in which a highly selective copper-based catalyst is employed may be represented by the following chemical equations:

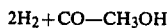

$$2H_2 + CO \rightarrow CH_3OH$$

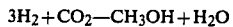

$$3H_2 + CO_2 \rightarrow CH_3OH + H_2O$$

The methanol synthesis gas mixture is usually prepared by steam reforming a methane-rich gas, such as natural gas or a refinery gas stream having a high methane content. In a methanol process where only steam reforming is used to produce the methanol synthesis gas mixture however, the synthesis gas mixture thus produced has an excess of hydrogen for the stoichiometry of the methanol synthesis reaction. Therefore to achieve a more optimum hydrogen/carbon oxides balance, if available, carbon dioxide is added to the methanol synthesis gas. However, since methanol is manufactured at elevated pressures and carbon dioxide is usually available only at lower pressures, an expensive compressor is required to compress the carbon dioxide to the operating pressure. In the process of the present invention, all the hydrogen produced by steam reforming of the methane-rich gas is used to produce methanol and does not require the added unit operation of adding carbon dioxide.

The supply of methanol synthesis gas may be alternately derived from other fossil fuel sources, i.e. heavy carbonaceous materials such as coal, coke, shale, naphtha and petroleum residues. A synthesis gas suitable for use in the production of methanol from such heavy carbonaceous materials can be obtained by high temperature partial oxidation using essentially pure oxygen. The partial oxidation of coal or coal gasification, such as processes using a Shell gasifier or a Texaco gasifier, are known in the art. However, a methanol process using a synthesis gas derived from such heavy carbonaceous materials alone is very expensive on the scale required for reasonably sized methanol plants. Further, the reliability of the partial oxidation process for on-stream performance is less than for steam reforming.

As the availability of natural gas decreases or it becomes more expensive, an alternate source of fossil fuel becomes necessary for the production of methanol synthesis gas. According to the process of the present invention, the advantages of the steam reforming process are maintained while integrating a second source of methanol synthesis gas produced by partial oxidation. Further, according to the process of the present invention the existing methanol plants now using the steam reforming of natural gas without supplemental feed of carbon dioxide may be modified to expand capacity to between 1.45 and 1.75 times existing capacity.

Referring to the FIGURE, natural gas is introduced by line 1 together with steam by line 2 into a steam reformer 3. Steam reforming is a conventional unit operation and known in the art. The conventional steam reformer is a furnace having a series of tubes filled with a nickel or treated nickel catalyst over which the natural gas passes and is converted into a mixture of gases. The mixture comprises hydrogen, carbon oxides, small amounts of unconverted hydrocarbons, mainly methane, and the inert gases nitrogen and argon. This mixture of gases is removed from the steam reformer 3 and passed through a heat exchanger for heat recovery and the condensed water is removed by line 4. The dry mixture of gases is then passed by line 5 to a gas compressor 6. The compressed gases pass through line 7 to a first methanol plant 8.

For the purposes of this patent, the methanol plant 8 is inclusive of a reactor or reactors which contain the methanol catalyst, the recycle sytem which recycles the unconverted gases through the reactor since only a percentage of the gas is converted to methanol on any pass through the reactor and all associated equipment to produce the crude methanol. Thus the term "methanol plant" as used herein is inclusive of all necessary equipment to produce the crude methanol. Usually included is purification equipment to produce high purity methanol such as a distillation system.

The methanol plant 8 may be represented by a low pressure methanol plant operating at synthesis pressures of 50-100 atmospheres and employing an ICI, Lurgi, or other copper-based methanol catalyst. The low pressure synthesis operating with a copper-based catalyst is generally in the temperature range of 240°-270° C. However, the specific reactor, catalyst or conditions are not material to the present invention and such are known in the art.

A purge is taken from methanol plant 8 by line 9. This purge is taken from the recycle loop to the reactor or reactors normally, to rid the system of the inert gases and excess hydrogen. The methanol plant 8 also produces a first methanol stream 10. In the process of the present invention, the purge gas stream 9 is used with a syn-gas stream produced by partial oxidation to feed a second methanol plant as will be described in more detail hereinafter.

A second source of hydrocarbon is employed to produce the methanol synthesis gas to feed a second methanol plant. The preferred heavy carbonaceous material is coal. Coal or coal plus water is fed by line 11, steam by line 12 and oxygen by line 13 to a coal gasifier 14. The gasifier is preferably a high temperature gasifier known in the art, e.g. a Shell gasifier, a Shell-Koppers gasifier or a Texaco gasifier. In these gasifiers a raw gas is produced, depending on the specific coal employed. The specific composition of the raw gas will vary; however, the gas is mostly carbon monoxide and hydrogen. The raw gas from the gasifier 14 will also contain some carbon dioxide and other acid gases besides the inert gases argon and nitrogen. For the purposes of this patent, the term "other acid gases" are the other acid gases besides carbon monoxide and carbon dioxide, such as the sulfur containing gases, i.e. $H_2S$ and COS, and cyanides. The other acid gases are all more selectively absorbed than the carbon oxides. The raw gas is passed through compressor 17 and line 18 into an acid gas removal system 19. The acid gas removal system 19 may be any of the well known absorbents, i.e. methanol, polyethylene glycol dimethyl ether, monoethanol amine(MEA)—diethanol amine(DEA), for acid gases and is operated to selectively absorb the other acid gases with some removal of carbon dioxide. The acid gases are usually removed by contacting or scrubbing the raw gas from the gasifier 14 with the absorbent in an absorption tower. The rich absorbent solution, i.e. the other acid gases containing absorbent, can be readily regenerated for reuse. The regeneration may be carried out in a stripper column where the rich absorbent solution is heated and/or reduced in pressure which separates the small amount of carbon dioxide and other acid gases from the absorbent. The small amount of carbon dioxide and other acid gases are removed from the acid gas removal system 19 by line 20.

The scrubbed gas is removed by line 21 and may be further compressed by passing through compressor 22. The compressed gas may be passed through a guard chamber 24 containing zinc oxide to remove any trace sulfur in the gases. Since sulfur in a poison to the methanol catalysts, the guard chamber 24 is a precautionary operation and other alternatives may be employed.

According to the present invention, the clear syn-gas, a gas which by its normal composition would not be a desirable syn-gas for methanol, from the guard chamber 24 is removed by line 25 and together with the purge gas in the stream 9 from the first methanol plant 8 is introduced by line 26 to a second methanol plant 27. The design capacity of the second methanol plant 27 is approximately 30 to 75 percent of the capacity of the first methanol plant 8. From the second methanol plant is produced a second methanol stream 28 and a purge stream 29 which may be used as fuel.

When maximum capacity of methanol is desired, an increase of over approximately fifty percent of the design basis of the first methanol plant 8, a high temperature shift unit operation 30 is included in the production of the syn-gas from the heavy carbonaceous material or coal feed. A line 31 passes the raw gas from gasifier 14 to the high temperature shift 30. The shift is carried out in a conventional manner by the addition of steam through line 32 which when passed over the known sulfur-resistant catalysts converts the carbon monoxide to carbon dioxide and hydrogen by the following well known shift reaction:

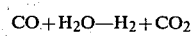

$$CO + H_2O \rightarrow H_2 + CO_2$$

Since this unit operation preceeds the acid gas removal system 19, the additional carbon dioxide produced by the high temperature shift 30 will be removed in system 19. The gas from the high temperature shift 30 is removed by line 33 and introduced behind a valve 34 in line 16. A valve 35 may be included in line 31. Valves 34 and 35 may be opened or closed so as to pass all or a portion or none of the raw gas from gasifier 14 through the high temperature shift 30.

A second embodiment of the present invention includes a line 36 with a valve 27 or other control means which takes a portion of the clear syn-gas in line 25 and introduces the gas to the first methanol plant 8. By introducing the clean syn-gas to the first methanol plant, an additional amount of methanol is produced since the composition of the combined gases is stoihcometrically more desirable. The second methanol plant 27 may then have a smaller design basis and still obtain the over all advantages of the present invention.

For a better unerstanding of the present invention, reference is had to the following specific example, which makes reference to the drawings.

3865 pound moles / hour (#mol/hr) of desulfurized natural gas, line 1 and 14228 #mol/hr of steam, line 2, are fed to a conventional steam reformer 3. The reforming is carried out over conventional nickel catalyst, and after waste heat recovery and condensing 9130 #mol/hr of water, line 4, dry reformed gas is available at 20 atmospheres (295 psia). The reformed gas, line 5, consists of 16271 #mol/hr of gas with a composition of 73.38 mol % $H_2$; 13.61 mol % CO; 8.98 mol% $CO_2$; 3.99 mol % $CH_4$ and 0.04 mol % $H_2$+ Ar. The reformed gas, line 5, is compressed by compressor 6 to 80 atmospheres (1176 psia) to provide feed gas, line 7, to a first methanol plant 8. Using a conventional ICI methanol catalyst and at low pressures (50–100 atmospheres) a crude methanol stream, line 10, consisting of 3492 #mol/hr of pure methanol together with 1376 #mol/hr of water and small amounts of other impurities is produced. The crude methanol stream 10 can be further purified by conventional distillation as desired.

A purge stream, line 9, is taken out of the first methanol plant 8 at about 80 atmospheres (1176 psia) to remove inerts in the recycle to the reactors. The inerts are methane, nitrogen and argon. The purge stream, line 9, contains 4419 #mol/hr gas having a composition: 81.01 mol % $H_2$; 2.22 mol % Co; 1.92 mol % $CO_2$; 14.71 mol % $CH_4$; and 0.14 mol % $N_2$+Ar.

In addition, 30130 #/hr of dry coal (Illonois No. 6), line 11, is introduced with 1409 #mol/hr of water or steam, line 12, and 917 #mol/hr of pure oxygen, line 13, to a gasifier 14. After waste heat recovery to raise steam and removal of 1124 #mol/hr of water, line 15, 2777 #mol/hr of raw gas is produced, line 16, with a composition: 34.93 mol % $H_2$; 42.92 mol % CO; 19.95 mol % $CO_2$; 0.32 mol % $CH_4$; 0.47 mol % $N_2$+Ar; and 1.41 mol % other acid gases, at a pressure of about 34.4 atmospheres (505 psia). The other acid gases are various sulfur and cyanide compounds. The raw gas, line 16, is compressed to 36.4 atmospheres (535 psia) by compressor 17 to provide a feed gas, line 18, to a conventional acid gas removal system 19 which removes 39 #mol/hr of other acid gases and some small amount of carbon dioxide, line 20. The sulfur compounds in the other acid gas are poisons to the methanol synthesis catalysts. The clean gas, line 21, is further compressed by compressor 22 to a pressure of 80.7 atmospheres (1186 psia). The compressed gas is passed over a zinc oxide (ZnO) guard bed in guard chamber 24 for trace sulfur compound removal. The clean syn-gas, line 25, consists of 2738 #mol/hr of gas with a composition: 35.43 mol % $H_2$; 43.54 mol % CO; 20.23 mol % $CO_2$; 0.32 mol % $CH_4$; and 0.48 mol % $N_2$+Ar. This clean syn-gas, line 25, is mixed with the purge gas stream from the first methanol plant, line 9, to give a total syn-gas, line 26, of 7157 #mol/hr, with a composition: 63.57 mol % $H_2$; 18.02 mol % CO; 8.93 mol % $CO_2$; 9.18 mol % $CH_4$ and 0.3 mol % $N_2$+Ar, which is introduced to the second methanol plant 27 at a pressure about 80 atmospheres (1176 psia).

The second methanol plant produces a crude methanol stream, line 28, consisting of 1703 #mol/hr methanol, 481 #mol/hr $H_2O$ plus small amounts of impurities. A purge stream is produced, line 29, with 1567 #mol/hr of gas having a composition: 42.31 mol % $H_2$; 4.34 mol % CO; 10.08 mol % $CO_2$; 1.22 mol % $N_2$+Ar and 42.05 mol % $CH_4$, which may be used as fuel.

The total pure methanol production from the integrated plants of the present invention is the sum of the pure methanol in the two crude product streams, lines 10 and 28, namely 5195 #mol/hr pure methanol.

The integrated plants of the present invention when compared to two separate plants for producing methanol assuming identical feed are substantially more efficient. For example, assuming 30130 #/hr of coal, if no shift reaction is carried out less than 700 #mol/hr of methanol can be produced, if technically the catalyst could withstand the poor synthesis gas produced. If to obtain a stoichiometrically acceptable gas, 544 #mol/hr of CO were shifted, line 31–33, and 1030 #mol/hr of $CO_2$ removed in the acid gas removal system 19, approximately 704 #mol/hr of methanol would be produced. Thus, the combined capacity of two independent plants would only yield 4197 #mol/hr. The integrated plants of the present invention represents a 23.8% increase over the independent plants based on the identical coal and natural gas feed.

Further, the integrated plants of the present invention take advantage of the on stream reliability of the processes which produce the methanol synthesis gas. The steam reforming process is better than 95% reliable whereas the coal gasification process is just over 80%. Thus, when the clean syn-gas from the coal gasification process is shut down, the first methanol plant of the present invention is not affected and may continue to operate under design conditions.

Still further, as illustrated by the example, the integrated plants of the present invention may be used with a steam reforming process and a coal gasification process where no shift reaction is carried out on the raw gas from the coal gasifier. The advantage is the elimination of an entire process unit and in addition a smaller acid gas removal system.

In summary, the present invention uses to a maximum advantage the steam reforming process and a oxidation process of converting a heavy carbonaceous material to produce synthesis gas which taken individually are not an optimum synthesis gas for methanol, and integrated the operations are such that an improved process for producing methanol is achieved.

We claim:

1. In a process for producing methanol which comprises converting a methane-rich gas by steam reforming into a mixture comprising hydrogen and carbon oxides and reacting said mixture in a first methanol plant which produces a methanol stream and a purge gas stream, the improvement to produce a total capacity of methanol between 1.45 and 1.75 of the design capacity of said first methanol plant comprising:

(a) converting by high temperature partial oxidation using essentially pure oxygen a heavy carbonaceous material into a raw gas comprising hydrogen, carbon monoxide, carbon dioxide, other acid gases and hydrocarbons;

(b) removing said other acid gases and trace elements of sulfur to produce a clean syn-gas; and (c) reacting said purge gas and said clean syn-gas in a second methanol plant to produce a second methanol stream.

2. A process for producing methanol according to claim 1 wherein the pressure in the methanol reactors of said first methanol plant is between 35 and 200 atmospheres and the pressure in the methanol reactors of said second methanol plant is between 30 and 190 atmospheres.

3. A process for producing methanol according to claim 1 wherein a portion of said clean syn-gas is reacted in said first methanol plant.

4. A process for producing methanol according to claim 1 wherein said second methanol plant produces a second purge gas stream which is used as fuel in the conversion of said methane-rich gas by steam reforming.

5. A process for producing methanol according to claim 1 wherein said first methanol plant is a pre-existing plant.

6. A process for producing methanol according to claim 1 wherein a high temperature shift step is between steps (a) and (b) which converts some of the carbon monoxide to hydrogen and carbon dioxide and removing said carbon dioxide produced.

7. A process for producing methanol according to claim 1 wherein there is no high temperature shift step between steps (a) and (b).

* * * * *